United States Patent
Greenberg et al.

(10) Patent No.: US 9,320,554 B2
(45) Date of Patent: Apr. 26, 2016

(54) WRIST FUSION PLATE

(71) Applicant: Stryker Trauma SA, Selzach (CH)

(72) Inventors: Jeffrey A. Greenberg, Carmel, IN (US); Tobias Bluechel, Selzach (CH); Philip Henry, Biel/Bienne (CH); Nina Kozic, Bern (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 354 days.

(21) Appl. No.: 13/713,605

(22) Filed: Dec. 13, 2012

(65) Prior Publication Data

US 2013/0165979 A1 Jun. 27, 2013

Related U.S. Application Data

(60) Provisional application No. 61/579,210, filed on Dec. 22, 2011.

(51) Int. Cl.
*A61B 17/80* (2006.01)

(52) U.S. Cl.
CPC .................................. *A61B 17/8061* (2013.01)

(58) Field of Classification Search
CPC ............................ A61B 17/80; A61B 17/8061
USPC ............................................ 606/60, 280–299
See application file for complete search history.

(56) References Cited

U.S. PATENT DOCUMENTS

| | | | |
|---|---|---|---|
| 5,066,296 A | 11/1991 | Chapman et al. | |
| 5,853,413 A * | 12/1998 | Carter et al. | 606/281 |
| 6,221,073 B1 | 4/2001 | Weiss et al. | |
| 6,623,486 B1 | 9/2003 | Weaver et al. | |
| 7,112,202 B2 | 9/2006 | Michelson | |
| 7,189,237 B2 | 3/2007 | Huebner | |
| 7,537,604 B2 | 5/2009 | Huebner | |
| 8,172,884 B2 | 5/2012 | Bouman | |
| 2004/0102775 A1 * | 5/2004 | Huebner | 606/69 |
| 2004/0102778 A1 | 5/2004 | Huebner et al. | |
| 2006/0173459 A1 | 8/2006 | Kay et al. | |

(Continued)

FOREIGN PATENT DOCUMENTS

| | | |
|---|---|---|
| EP | 2158864 A2 | 3/2010 |
| FR | 2556583 A1 | 6/1985 |

OTHER PUBLICATIONS

"Wrist Arthrodesis in Rheumatoid Arthritis"—Pech, et al—Journal of Bone & Joint Surgery, vol. 78-B, No. 5, Sep. 1996.

(Continued)

*Primary Examiner* — Christopher Beccia
(74) *Attorney, Agent, or Firm* — Lerner, David, Littenberg, Krumholz & Mentlik, LLP

(57) ABSTRACT

A wrist fusion plate has a proximal portion comprising at least one opening, wherein the proximal portion attaches to the radius by inserting bone screws through the proximal portion opening. A distal plate portion has a plurality of openings and is adapted to be attached to a metacarpal (M) by inserting bone screws through the distal portion attachment openings and into the metacarpal. A central plate portion has at least one attachment opening and is adapted to be attached to a carpal bone by inserting bone screws through the attachment opening. The proximal and distal portions are aligned along a longitudinal axis of the wrist fusion plate. One of the distal portion attachment openings is elongated in a direction perpendicular to the longitudinal axis.

16 Claims, 12 Drawing Sheets

(56) References Cited

U.S. PATENT DOCUMENTS

2007/0233114 A1* 10/2007 Bouman .................. 606/69
2007/0270850 A1   11/2007 Geissler
2012/0215223 A1   8/2012 Chiodo et al.

OTHER PUBLICATIONS

A New Approach to Wrist Arthrodesis—Synthes—c1994.
Internal Fixation of Small Frac.—Heim et al—Springer-Verlag Berlin Heidelberg—3rd ed, c1988,pp. 151,160,176,177,178.
LCP Wrist Fusion Set. Anatomic Plates for Total Wrist Fusion, Synthes, Dec. 2008.
May.TM. Anatomical Bone Plates—Link America, Inc.—JBJS Sep. 1996.
Osteotomy System—The Complete Knee Solution—Zimmer, Inc.—c1994—Literature No. 97-5250-101.
The Indiana Hand Center Newsletter, Foundation for Hand Research & Education, vol. 1, Issue 2, Fall 1993.
Trauma Locking Plate and Screws, TST Tibbi Alethler San. Ve Tic. Ltd. Sti., 2009.
Extended European Search Report for Application No. EP12008497 dated Feb. 27, 2013.

* cited by examiner

WRIST FUSION PLATE

CROSS-REFERENCE TO RELATED APPLICATION

The present application claims the benefit of the filing date of U.S. Provisional Patent Application No. 61/579,210 filed Dec. 22, 2011, the disclosure of which is hereby incorporated herein by reference.

BACKGROUND OF THE INVENTION

The present disclosure generally relates to a plate for application to a wrist joint for use in an orthopaedic procedure, and, more particularly, to a wrist fusion plate for use in fusing a wrist joint. The wrist fusion plate may be applicable for correction of bone deformation due to arthritis, rheumatoid arthritis, inflammatory diseases such as rheumatic fever or tuberculosis, genetic disorders of the bone, or for setting a wrist fracture.

In the field of treating wrist disorders (e.g., surgical procedures for realigning misaligned or deformed wrist bones), a surgeon implants a wrist plate and attaches one or several bone attachment members into desired locations on the bones of the wrist through the wrist plate The wrist plate is thus fixed in the desired position such that the bones of the wrist have desired orientations with respect to each other.

However, proper alignment of the bones of the wrist can be very difficult, and any misalignment can result in severe pain to the patient, especially when attempting to use the hand, and may also result in improper healing or fusion of fractured or treated bones of the wrist. Additionally, the intricate network of tendons, muscles, and nerve endings in the wrist joint and the area of the hand can make proper fixation difficult, as the surgeon must be careful not to damage surrounding tissues as much as possible when fixing the wrist plate.

U.S. Pat. No. 5,853,413 discloses a wrist plate having portions configured to be attached to a radius and a metacarpal bone. A central portion of the wrist plate is saddle-shaped and configured to be attached to various bones of the wrist, such as the capitate, scaphoid, hamate, triquetrum, and lunate bones. The portion of the plate to be attached to the metacarpal bone is inclined with respect to the portion of the plate to be attached to the radius, such that dorsal flexion of the metacarpal bone with respect to the carpal bones results. The portion of the plate to be attached to the metacarpal bone may also be inclined with respect to the portion of the plate to the attached to the radius in a perpendicular plane, such that ulnar or radial deviation of up to 30 degrees is provided.

When performing an operation of fixing the wrist, proper orientation and positioning of the metacarpal bones with respect to the radius is desired to allow the patient maximum possible usage of the fixed wrist with minimal pain. However, known wrist fusion plates have disadvantages in that it is difficult to position and fix the bones of the wrist and hand in an optimal orientation, as the wrist fusion plates typically have a predefined ulnar/radial deviation and a predefined dorsal/palmar flexion. Therefore, when a patient has an unusual anatomy due to deformation, whether rheumatoid, genetic, or post-traumatic, it can be difficult to obtain an optimal metacarpal orientation with existing wrist fusion plates.

BRIEF SUMMARY OF THE INVENTION

It is therefore one aspect of the invention to provide a wrist fusion plate that can be adaptively used by a surgeon to obtain an optimal wrist orientation. It is a further aspect to provide a method of implanting a wrist fusion plate onto a wrist of a patient, whereby optimal wrist orientation can be achieved.

According to one aspect a wrist fusion plate is provided, comprising a proximal portion comprising at least one proximal portion attachment opening, wherein the proximal portion is adapted to be attached to a radius of the patient by inserting a bone attachment member through the at least one proximal portion attachment opening and into the radius, a distal portion comprising a plurality of distal portion attachment openings and adapted to be attached to a metacarpal of the patient by inserting bone attachment members through the distal portion attachment openings and into the metacarpal; and a central portion comprising at least one central portion attachment opening and adapted to be attached to a carpal bone of the patient by inserting a bone attachment member through the central portion attachment opening, wherein the proximal portion and distal portion extend generally along a longitudinal axis of the wrist fusion plate, and wherein one of the distal portion attachment openings is an oblong distal portion attachment opening that is elongated in a direction substantially perpendicular to the longitudinal axis.

The central portion may comprise a distal central portion which inclines in a palmar direction from the distal portion, and a proximal central portion which inclines in a palmar direction from the proximal portion such that the central portion is bent in a palmar direction from the longitudinal axis. The central position may have a U-shaped or flattened U-shaped form.

The at least one central portion attachment opening adapted to be attached a carpal bone of the patient may be adapted to be attached to a capitate of the wrist of the patient. The central portion may further comprise a second central portion attachment opening configured to be fixed to a distal surface of the radius of the patient. Alternatively, the central portion attachment openings may be configured to be attached to various carpal bones of the wrist.

The central portion, alternatively, may be generally straight, and the distal, proximal, and central portions may extend generally along the longitudinal axis. Further, the central portion may comprise two central portion attachment openings adapted to be attached to carpal bones, wherein a first central portion attachment opening may be configured to be attached to a capitate of the wrist of the patient, and a second central portion attachment opening may be configured to be attached to a scaphoid of the wrist of the patient.

The proximal portion may comprise a plurality of proximal portion attachment openings. In one embodiment, one of the plurality of proximal portion attachment openings may be an oblong proximal portion attachment opening that is elongated in a direction parallel to the longitudinal axis. A bone plate having two oblong openings oriented 90° to one another is shown in U.S. Pat. No. 8,172,884.

The oblong distal portion attachment opening may have a length in the direction perpendicular to the longitudinal axis within a range of approximately 2.0 mm to 4.0 mm. For example, the oblong distal portion attachment opening may have a length in the direction perpendicular to the longitudinal axis of approximately 3.0 mm. The oblong proximal portion attachment opening may have a length in the direction parallel to the longitudinal axis within a range of approximately 3.0 mm to 5.0 mm. For example, the length of the oblong distal portion attachment opening in the direction perpendicular to the longitudinal axis may be approximately 4.0 mm.

One or more distal portion attachment openings other than the oblong distal portion attachment opening may be circular distal portion attachment openings. The other distal portion attachment openings may have a diameter within a range of approximately 2.0 to 3.5 mm. For example, they may have a diameter of approximately 2.7 mm. The proximal portion attachment openings other than the oblong proximal portion attachment opening may have a diameter within a range of approximately 2.7 to 4.0 mm. For example, they may have a diameter of approximately 3.5 mm.

The sizes and diameters of the oblong and circular attachment openings, as well as other dimensions of the wrist fusion plate, may be further adapted to the size of the bone to which the plate is to be attached. For example, a wrist fusion plate to be applied to a child's hand may be dimensioned to be smaller than the dimensions of a standard configuration of the wrist fusion plate.

A length of the oblong distal portion attachment opening may be greater than a width of the distal portion adjacent to the oblong distal portion attachment opening. As an example, protrusions may be provided to the distal portion in the region of the oblong distal portion attachment opening to allow the distal portion to accommodate the oblong distal portion attachment opening.

The at least one proximal portion attachment opening, the plurality of distal portion attachment openings, and the at least one central portion attachment opening may be provided aligned along the longitudinal axis. Alternatively, one or more of these openings may be provided with an offset relative to the longitudinal axis.

The bone attachment members may be bone screws. Alternatively, the bone attachment members may be realized, for example, in the form of K wires, bone pegs or bone nails. At least one of the attachment openings may be recessed, for example so as to receive the bone attachment members such that the bone attachment members protrude by an amount less than a thickness of a head portion of the bone attachment member or do not protrude at all over a dorsal surface of the wrist fusion plate when implanted onto the wrist of the patent. If the bone attachment members are bone screws, the bone screws may be adapted to be implanted using standard or specialized screwdriver bits.

A method of implanting a wrist fusion plate is further provided, comprising the steps of implanting a first bone attachment member into the metacarpal through the oblong distal portion attachment opening, implanting a second bone attachment member into the radius through at least one proximal portion attachment opening, adjusting the orientation of the metacarpal with respect to the radius by sliding the first bone attachment member within the oblong distal portion attachment opening, and implanting a third bone attachment member into the at least one distal portion attachment opening that is not the oblong distal portion attachment opening. The method may further comprise the steps of, before implanting the second and third bone attachment members, inserting a fourth bone attachment member into the radius through the oblong proximal portion attachment opening, and adjusting an amount flexion of the wrist of the patient by sliding the fourth bone attachment member within the oblong proximal portion attachment opening.

An alternate method of implanting a bone plate having both a proximal slot aligned with the plate longitudinal axis and a more distal slot located over a metacarpal bone and oriented in a direction perpendicular to the longitudinal axis of the bone plate can be used. Initially in this method a k wire is placed through a proximal circular hole which is located more proximal than the bone plate slot aligned with a longitudinal axis of the plate. This hole may be the most proximal hole in the wrist plate. With the k wire in place a compression screw is placed in the elongated compression slot in the proximal portion of the bone plate and the screw is left loose. A bone screw is then placed in the more distal elongated gliding slot which extends perpendicular to the bone plate longitudinal axis into the metacarpal bone in a central or neutral position in the slot. This screw is also left loose. The surgeon then rotates the hand to a desired position and tightens the bone screw in the elongated gliding slot. Typically the plate has two or three distal circular holes more distal than the elongated gliding slot which bores are located over the metacarpal bone. Screws are inserted and tightened into these holes after the screw and the elongated gliding hole is tightened. These holes are located in the plate intermediate the axially aligned slot and a concave bend in the plate. The k wire is then removed and the compression screw and the proximal elongated slot is tightened. Typically there are one or two circular holes distal of the elongated slot aligned with the plate axis and these are then inserted and tightened. The k wire is then removed from the proximal most circular hole and a screw is inserted and tightened. Finally a locking screw is inserted through a locking bore in the plate proximal of the elongated gliding bore in the area of the capitate bone and this screw is tightened.

The wrist fusion plate and method may, for example, be employed to treat disorders of the wrist, such as rheumatoid arthritis or congenital bone disorders. However, the method may also be employed to treat deformative conditions such as tuberculosis of the bone, or to repair damage to the wrist caused by trauma.

BRIEF DESCRIPTION OF THE DRAWINGS

The foregoing objects, features, aspects and advantages will become more apparent from the following detailed description when taken in conjunction with the accompanying drawings.

DETAILED DESCRIPTION

Figure 1:
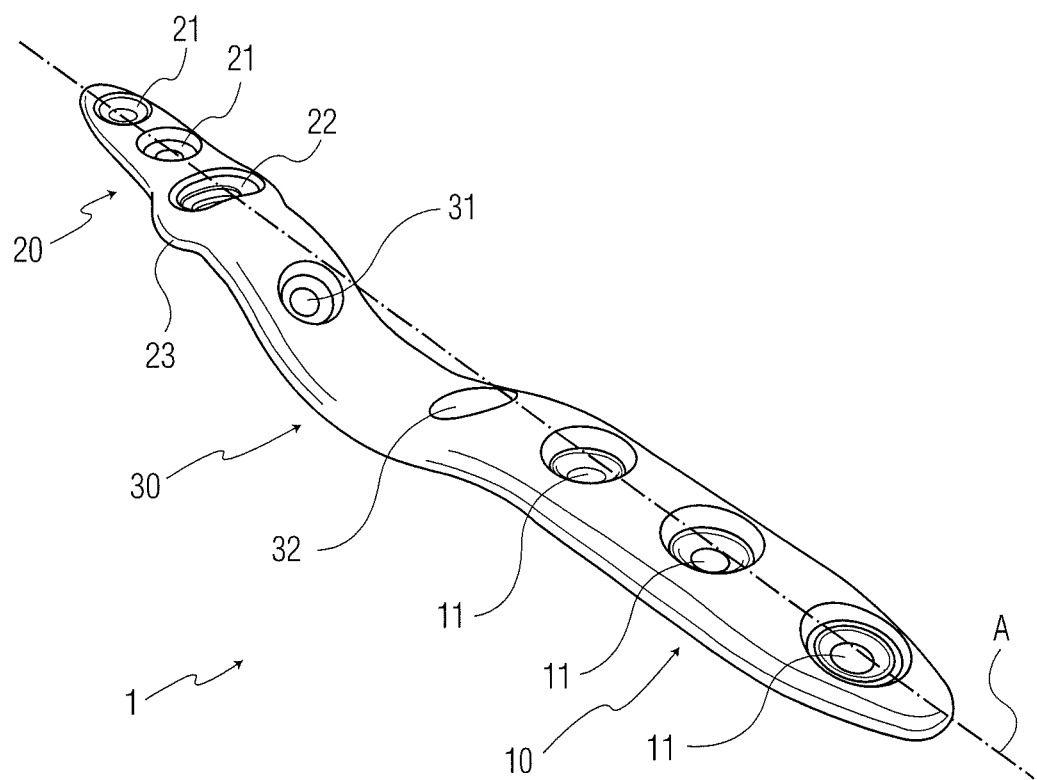
FIG. 1 is a perspective view showing a first embodiment of the wrist fusion plate.

Hereinafter, embodiments of the wrist fusion plate will be described with reference to the accompanying figures. The same reference numerals are used to refer to identical or similar elements. In the following, the term "distal" refers to a direction toward a patient's fingertips, and the term "proximal" refers to a direction toward a patient's radius and ulna.

FIG. 1 shows a perspective view of a first embodiment of the wrist fusion plate 1. The wrist fusion plate 1 comprises a proximal portion 10, a distal portion 20, and a central portion 30. The proximal portion 10 is sized and shaped to be attached to a radius of the patient. The distal portion 20 is sized and shaped to be attached to a metacarpal bone of the patient. Moreover, the central portion 30 is sized and shaped to be attached to at least one carpal bone of the patient's wrist. Specifically, the central portion 30 may be sized and shaped to be attached to a capitate bone of the carpal bones. The distal and proximal portions 10, 20 extend along a common longitudinal axis A of the wrist fusion plate 1. The wrist fusion plate 1 is sized and shaped to be implanted onto a patient's wrist with the proximal, distal, and central portions 10, 20, 30 attached to the radius, metacarpal, and carpal bones, respectively, such that a total wrist fusion is accomplished.

The proximal portion 10 may comprise three proximal portion attachment openings 11. The proximal portion attachment openings 11 extend along the longitudinal axis A and are generally spaced at approximately constant intervals. The proximal portion attachment openings 11 have a circular shape and are configured to receive bone attachment members 40 such as bone screws or pins (see FIG. 2). While the proximal portion 10 has a substantially constant width and thickness, a proximal end of the proximal portion 10 may be tapered toward the longitudinal axis A.

The distal portion 20 comprises a plurality of distal portion attachment openings 21, 22. The distal portion attachment openings 21, 22 extend generally along the longitudinal axis A, and are spaced at generally constant intervals. The distal portion attachment openings may comprise two circular distal portion attachment openings 21 and an oblong distal portion attachment opening 22 configured to receive bone attachment members 40 (see FIG. 2).

The oblong distal portion attachment opening 22 is elongated in a direction transverse to and preferably perpendicular to the longitudinal axis A. The oblong distal portion attachment opening 22 may have a length in the elongated direction (that is, in the direction perpendicular to the longitudinal axis A) of approximately 3.0 mm. The length of the oblong distal portion attachment opening 22 in the elongated direction is larger than a diameter of the bone attachment member that the oblong distal portion attachment opening 22 is configured to receive. Such a dimensioning will allow guided movement of the wrist fusion plate 1 while the bone attachment member 40 is disposed within the oblong distal portion attachment opening 22 as will be explained in greater detail below.

The distal portion 20 may generally be tapered toward the longitudinal axis A. As shown in FIG. 1, the width of the distal portion 20 is smaller than the length of the elongated oblong distal portion attachment opening 22. The distal portion 20 includes protrusions 23 that allow the oblong distal portion attachment opening 22 to be completely accommodated within the distal portion 20.

The central portion 30 comprises a plurality of central portion attachment openings 31, 32. The distal-most central portion attachment opening is a capitate central portion attachment opening 31, and is positioned on the wrist fusion plate 1 so as to be attached to the capitate bone of the carpal bones when the wrist fusion plate 1 is implanted onto the patient's wrist. The proximal-most central portion attachment opening is a radial central portion attachment opening 32 and is positioned on the wrist fusion plate 1 so as to be attached to a distal portion of the radius.

The central portion 30 is curved with respect to the longitudinal axis A, such that, from the proximal portion 10 and the distal portion 20, the central portion inclines downwardly (that is, in a palmar direction) in the form of a flattened U. For example, the central portion 20 may incline downwardly from the proximal portion 10 at an angle of approximately 10 to 20 degrees, and may incline downwardly from the distal portion 20 at an angle of approximately 10 to 20 degrees. The capitate central portion attachment opening 31 is disposed on a portion of the central portion 30 that inclines downwardly from the distal portion 20, such that, when implanted onto the capitate C (see FIG. 2), the capitate C is fixed in a state of dorsal abduction with respect to the radius. The radial central portion attachment opening 32 is disposed on a portion of the central portion 30 that inclines downwardly from the proximal portion 20, and is positioned so as to be attached to a distal surface of the radius R.

The wrist fusion plate 1 may be comprised of titanium or any other biocompatible material. Alternatively, the wrist fusion plate 1 may be comprised, in full or in part, by a bio-absorbable material, for example, when the wrist fusion plate 1 is installed to treat a traumatic wrist breakage. In such a case, it may be possible to avoid the need to later remove the wrist fusion plate 1 after the fracture has healed. The bone attachment members 40 may be bone screws, and have various diameters adapted to be received within the attachment openings 11, 21, 22, 31, 32 so as to fix the wrist fusion plate 1 to the patient's bones.

The attachment openings 11, 21, 22, 31 are each sunken so as to receive a bone attachment member 40 such that the bone attachment member 40 protrudes minimally or does not protrude over the upper surface of the wrist fusion plate 1 when implanted onto a patient's wrist. The proximal portion attachment openings 11 and the central portion radial attachment portion 32 may have identical diameters. Sizes and diameters of the attachment openings and the bone attachment members 40 may be selected according to the size and shape of the bones to which the corresponding portions of the wrist fusion plate 1 are to be attached. For example, the proximal portion attachment openings 11 and the central portion radial attachment portion 32 may have diameters of 3.5 mm, or, more generally, may have diameters within a range of approximately 2.7 to 4.0 mm. The circular distal portion attachment openings 21 and the capitate central portion attachment opening 31 may have identical diameters, and may have diameters of 2.7 mm, or, more generally within a range of approximately 2.0 to 3.5 mm. The oblong distal portion attachment opening 22 may have a dimension in the direction of the longitudinal axis A that is configured to receive a bone attachment member 40 having a diameter equal to the bone attachment member 40 configured to be received by the circular distal portion attachment openings 21. Alternatively, the oblong distal portion attachment opening 22 may be configured to receive a bone attachment member 40 having a smaller diameter than the diameter of the bone attachment member 40 configured to be received by the circular distal portion attachment openings 21. For example, the oblong distal portion attachment opening 22 may be configured to receive a bone attachment member 40 having a diameter of 2.0 mm. Alternatively, the oblong distal portion attachment opening 22 may be configured to receive a bone attachment member 40 having a diameter within a range of approximately 1.5 to 2.7 mm.

Because the oblong distal portion attachment opening 22 is configured to receive a bone attachment member 40 in a sliding state, wherein final fixation of the wrist fusion plate 1 with respect to the metacarpal M is provided by the circular distal portion attachment openings 21, the diameter of the bone attachment member 40 received by the oblong distal portion attachment opening 22 may be able to be reduced, while still providing adequate fixation to the metacarpal M to allow sliding of the wrist fusion plate 1 thereon. A smaller bone attachment member 40 may actually result in an increased ability to easily slide the wrist fusion plate 1 on the metacarpal M via the oblong distal portion attachment opening 22. By sizing the bone attachment members 40 to be as small as possible with respect to their function and the bone to which they are attached, pain experienced by the patient and recovery time may be reduced.

A length of the proximal portion 10 may generally be within a range of approximately 40 to 50 mm. A length of the distal portion 20 may generally be within a range of approximately 35 to 40 mm. A length of the central portion 30 may generally be within a range of approximately 30 to 40 mm. More specifically, the length of the central portion 30 which inclines downwardly from the proximal portion 10 may generally be within a range of approximately 15 to 20 mm, while the length of the central portion 30 which inclines downwardly from the distal portion 20 may generally be within a range of approximately 15 to 20 mm.

Figure 2:
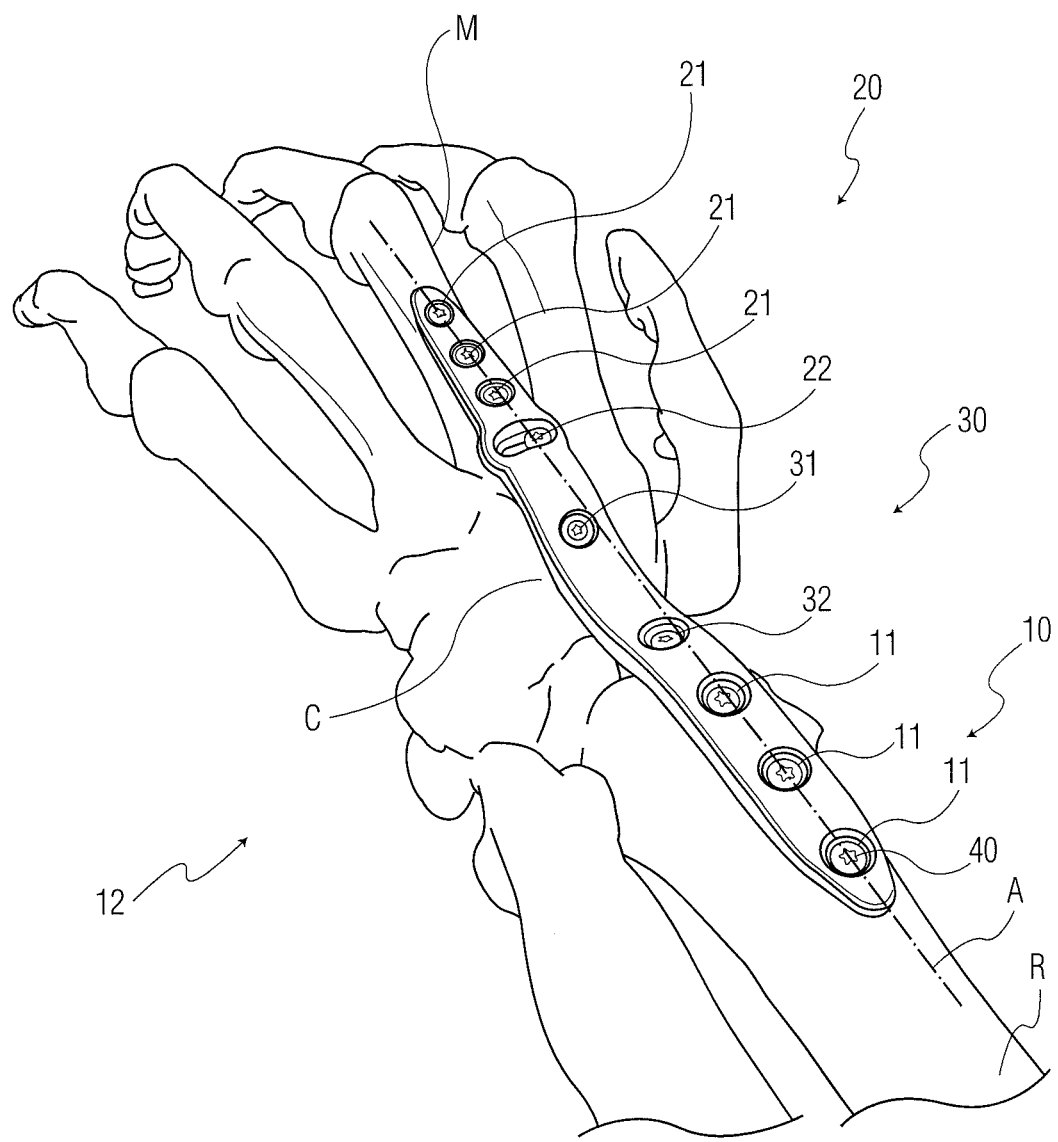
FIG. 2 is a perspective view showing a view of the first embodiment of the wrist fusion plate implanted onto a wrist.

Having described the configuration of a first embodiment of the wrist fusion plate 1 with reference to FIG. 1, a method of implanting the wrist fusion plate 1 in a wrist fusion operation will be described with respect to FIG. 2.

First, the surgeon prepares a wrist site to receive the wrist fusion plate 1 for implantation of the wrist fusion plate 1. An incision is made into the skin to expose the site. If necessary, the bone tissue itself may be treated, by removing degenerated bone tissue and cartilage and/or implanting bone tissue to supplement deteriorated or degenerated bone tissue. For example, cancellous bone tissue may be implanted to improve the structure and shape of the bones of the wrist.

When attaching the wrist fusion plate 1, the surgeon first implants the bone attachment member 40 through the oblong distal portion attachment opening 22 and into the metacarpal M, and tightens the bone attachment member 40 such that the wrist fusion plate 1 can still be slid side to side under the influence of an applied force, while, without the application of an outside force, the wrist fusion plate is still generally fixed with respect to the metacarpal M. Thereafter, or earlier, the surgeon implants a bone attachment member 40 in the radius R through one of the proximal portion attachment members 11, thereby fixing the wrist fusion plate 1 to the radius R. In order to adjust the rotation of the wrist and the radial/ulnar abduction of the wrist, the surgeon my adjust the exact positioning of the metacarpal M with respect to the radius R by sliding the bone attachment member 40 inserted into the metacarpal M within the oblong distal portion attachment opening 22. Thereby, the surgeon may achieve a desired ulnar/radial rotation of the wrist. As an example, the surgeon may position the bone attachment member 40 within the oblong distal portion attachment opening 22 to achieve an ulnar abduction of approximately 5 to 10 degrees.

When a desired orientation of the metacarpal M with respect to the radius R is achieved, the surgeon may implant bone attachment members 40 into the central portion attachment openings 31, 32, thereby attaching the wrist fusion plate 1 to the capitate C and a distal surface of the radius R, respectively. By controlling the positions at which the bone attachment members 40 are implanted into the capitate C and the distal surface of the radius R, the surgeon can fix the dorsal/palmar orientation of the wrist in a desired orientation, for example, to produce a dorsal flexion in a desired amount. The wrist may be fixed having a dorsal flexion of approximately 10 to 15 degrees.

By judging the direction in which the metacarpal M should be moved, and placing the bone attachment member 40 into an opposite side of the oblong distal portion attachment opening 22, the surgeon can easily obtain the desired position of the metacarpal M. For example, if the metacarpal needs to be moved leftward in order to obtain the desired orientation, the surgeon may implant the bone attachment member 40 into a right-most portion of the oblong distal portion attachment opening 22, such that the metacarpal M may thereafter be moved in a leftward direction.

Thereafter, the surgeon may implant bone attachment members 40 in the remaining proximal portion attachment openings 11. Alternatively, the surgeon may install the bone attachment members 40 in each of the proximal portion attachment openings 11 consecutively, that is, all proximal portion attachment openings may be attached to the radius R in a single step before attaching the wrist fusion plate 1 to the radius R via the oblong distal portion attachment opening 22.

It is noted that the above described method steps may be performed in any order, so long as the bone attachment members 40 implanted into the distal portion attachment openings 21 are implanted after a bone attachment member 40 is installed into the oblong distal portion attachment member 22.

As will be appreciated, by providing the oblong distal portion attachment opening 22, an exact desired orientation of the metacarpal M with respect to the radius R can be achieved, while moving the bone attachment member 40 within the oblong distal portion attachment opening 22. At the same time, while adjusting the orientation of the wrist and the ulnar/radial abduction, the positioning of the wrist fusion plate 1 with respect to the radius R can be held constant, when changing the position of the wrist fusion plate 1 on the metacarpal M by very small degrees. This allows for a fine adjustment of the positioning of the metacarpal M with respect to the radius R, which would be difficult to achieve by simply manually moving the bones on the surgical site.

The presence of muscle tissue, tendons, nerves, cartilage, and other tissue in the area of the surgical site may make it difficult to reposition and hold steady a desired orientation of the wrist. Further, due to various possible deformities of the bone tissue to which the wrist fusion plate 1 is attached, it may be difficult to properly align the bones without mechanical assistance, and it may be difficult to judge a final orientation produced by attachment of the wrist fusion plate 1 due to the influence of an irregular bone surface or compression of bone tissues. In any of these cases, with the wrist fusion plate 1 of the present disclosure, the surgeon is provided with the ability to finely adjust the position of the wrist fusion plate 1 with respect to the metacarpal M by sliding the bone attachment member 40 within the oblong distal portion attachment opening 22.

In one application, if the wrist in its natural pre-corrected orientation has an abnormal orientation of the metacarpal 11 such that it is difficult for the surgeon to manually orient the metacarpal M in the desired position, the surgeon can judge the direction in which the metacarpal M should be moved in order to achieve a desired orientation, and can implant the bone attachment member 40 through the oblong distal portion attachment opening 22 such that the desired direction of movement can be achieved while the bone attachment member 40 is implanted into the metacarpal M through the oblong distal portion attachment opening 22. As such, the surgeon may be able to, by sliding the wrist fusion plate 1 via the bone attachment member 40 in the oblong distal portion attachment opening 22, achieve a better orientation of the metacarpal M than would be possible by simply manually positioning the bones before implantation of the bone attachment members 40.

In addition to providing the surgeon with the ability to finely adjust the orientation of the metacarpal M with respect to the radius R, the further advantage is achieved that a number of holes that must be drilled into the metacarpal M may be reduced. For example, in the known wrist fusion plates, if the surgeon needs to adjust the orientation of the metacarpal M after implanting a first bone attachment member into the metacarpal M, the bone attachment member must be removed, the wrist fusion plate must be moved to the desired orientation, and a further bone attachment member must installed into the desired location. Thus a larger number of holes is drilled in the metacarpal M than necessary for receiving the final number of bone attachment members, which is damaging the bone tissue (and which may already be partially decomposed or deformed) and causes a larger amount of pain for the patient and the susceptibility to infection and further loss of bone tissue. Further, the removal of a misplaced bone attachment member may cause the metacarpal M to change its orientation from the previously fixed orientation, as it returns to its normal orientation. This may cause the surgeon to lose track of the desired implantation site of the bone attachment member.

Additionally, even if the orientation of the metacarpal M and the desired adjusted location for the bone attachment member can be maintained, the problem is still present that fine adjustment of the position of the metacarpal M cannot be achieved. Specifically, if the surgeon wishes to move the metacarpal M by only a small amount, it may be necessary in order to achieve the desired rotation to insert a bone attachment member very close to the initial attachment site, or, even worse, the hole for the bone attachment member may partially overlap the initial attachment site. As such, it may be impossible for the surgeon to insert the bone attachment member in the desired location, if the holes in the bone for receiving the bone attachment members are too close together or overlap. Therefore, in the wrist fusion plates of the prior art, if the surgeon does not obtain the correct position of the metacarpal M in with the first bone attachment member, it may not be possible to thereafter adjust the orientation of the metacarpal M with respect to the radius.

Because the rotation of the wrist has a significant impact on the pain experienced by the patient and the usability of the fused wrist, fine adjustment of this orientation provides the surgeon with the ability to provide the patient with the most comfortable and usable fused wrist orientation. Additionally, even if the surgeon were able to adjust the position of the metacarpal M with the known wrist fusion plates of the prior art by providing attachment sites a sufficient distance away from each other, the disadvantage is still provided by the known prior art wrist plate that a large amount of time required for the adjustment of the bone attachment member position is required. In a case in which the attachment sites must be tapped before implantation of the bone attachment members, the wrist plate may actually have to be completely removed in order to tap the new hole for the adjusted bone attachment member position. In contrast, according to the wrist fusion plate 1 described in the present disclosure, a surgeon is provided with the ability to finely tune an orientation of the metacarpal M with respect to the radius R, without having to remove the bone attachment member or the wrist plate 1, and without having to drill more attachment holes than necessary.

Therefore, the wrist fusion plate 1 and the method of implanting the wrist fusion plate 1 described above provide significant advantages over the known wrist fusion plates of the prior art.

A second embodiment of a wrist fusion plate 2 will now be described with respect to FIG. 3. Elements of the second embodiment that are identical or similar as those described with respect to the first embodiment are not specifically discussed. Each of the features and alternatives described with respect to the first embodiment are applicable to and can be combined with the features of the second embodiment.

Figure 3:
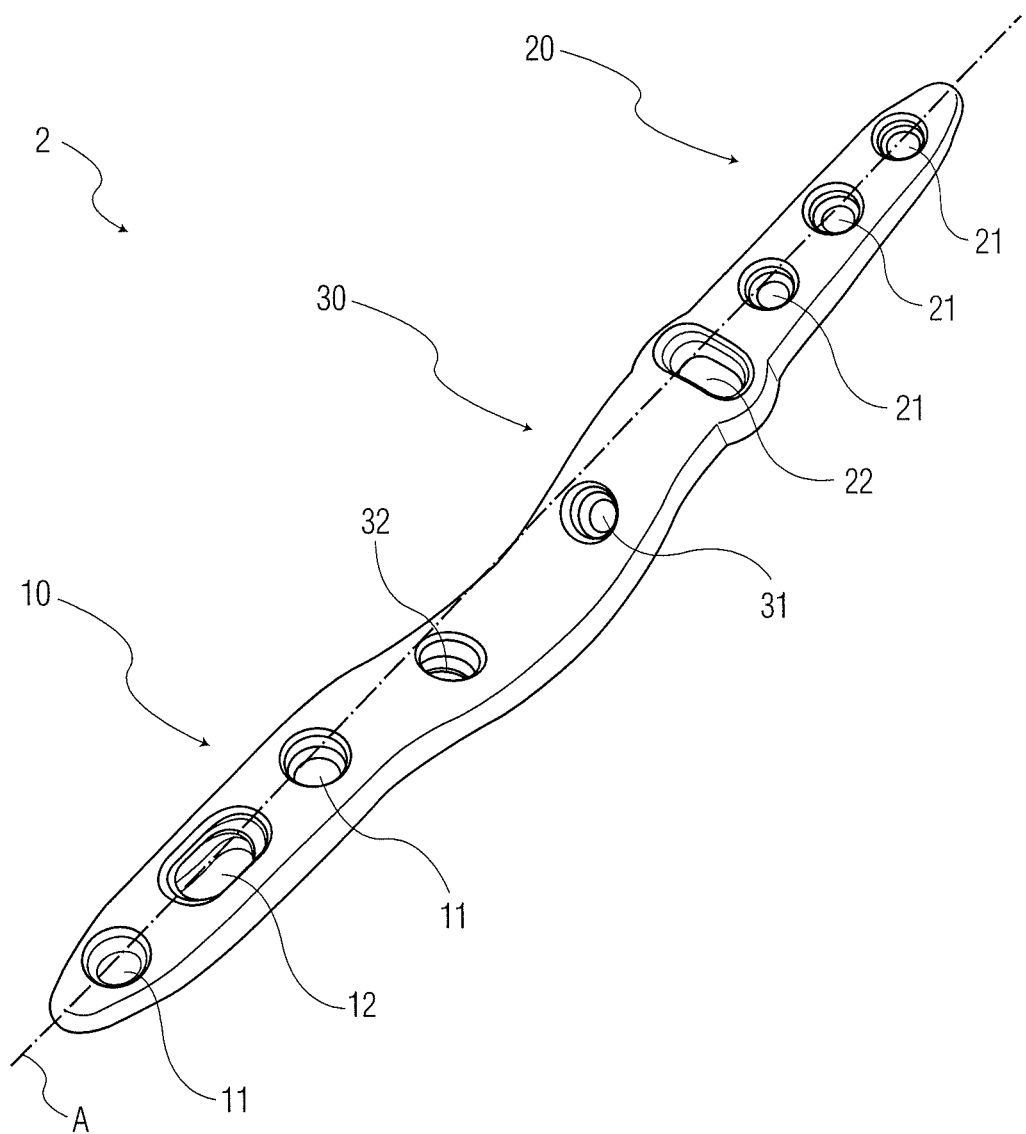
FIG. 3 is a perspective view showing a second embodiment of the wrist fusion plate.

As illustrated in FIG. 3, the wrist fusion plate 2 of the second embodiment is similar to the wrist fusion plate 1 of the first embodiment, except that the wrist fusion plate 2 of the second embodiment further comprises an oblong proximal portion attachment opening 12 instead one of the circular proximal attachment openings 11 of the first embodiment. The oblong proximal portion attachment opening 12 is elongated in a direction perpendicular to the longitudinal axis A of the wrist fusion plate 2. The oblong proximal portion attachment opening 12 may have a length in the elongated direction (that is, in the direction parallel to the longitudinal axis A) of approximately 4.0 mm (and generally within a range of approximately 3.0 mm to 5.0 mm). The oblong proximal opening may be located between circular openings such as the proximal most opening shown in FIG. 3.

By additionally providing the oblong proximal portion attachment opening 12, the surgeon can adaptively adjust not only the orientation of the metacarpal M, but can also adjust the position of the proximal portion 10 on the radius R, and, thereby, the amount of flexion in the wrist (specifically, the amount of dorsal flexion in the carpal bones) by sliding a bone attachment member 40 within the oblong proximal portion attachment opening 12.

When implanting the wrist fusion plate 2, the surgeon may provisionally provide a bone attachment member 40 into the oblong proximal portion attachment opening 12. Then, by sliding the bone attachment member 40 within the oblong proximal portion attachment opening 12, the amount of flexion of the wrist can be finely adjusted. For example, by sliding the wrist fusion plate proximally or distally, the point at which the central portion attachment openings 31, 32 contacts the distal surface of the radius R and the capitate C, respectively, can be finely adjusted in order to achieve the desired orientation of the capitate C with respect to the radius R. Then, bone attachment members 40 may be implanted into the circular proximal portion attachment openings 21 to fix the position in the longitudinal direction of the wrist fusion plate 2 with respect to the radius R.

The surgeon may implant bone attachment members 40 into the oblong distal portion attachment opening 22 and the oblong proximal portion attachment opening 12 consecutively, and may adjust the flexion of the wrist while the bone attachment member 40 is inserted into the metacarpal M. In this manner, a more predictive orientation of the final orientation can be achieved, because of the fixed position in the longitudinal direction of the bone attachment member 40 in the oblong distal portion attachment opening 22, which may make the operations of aligning the wrist fusion plate 2 for implantation of the bone attachment members 40 into the central portion attachment openings 31 and 32 easier.

As with the oblong distal portion attachment opening 22, the oblong proximal portion attachment opening 12 provides the advantages that fine-tuning of the flexion of the wrist can be achieved by moving the wrist fusion plate 2 relative to the inserted bone attachment member 40 by small amounts. Also, by implanting the bone attachment member 40 in the oblong distal portion attachment opening 22 before adjusting the wrist flexion, a secure positioning of the wrist fusion plate 2 with respect to the distal surface of the radius and the capitate C can be obtained, and the final wrist flexion can be visualized before insertion of bone attachment members 40 into the central portion attachment openings 31, 32. The advantages provided by the oblong proximal portion attachment opening 12 are similar to those provided by the oblong distal portion attachment opening 22, namely, that fine adjustment can be achieved without having to drill additional holes in the bone for adjusted bone attachment member positions, and that the wrist fusion plate 2 can actually be used to manually urge the radius R, the metacarpal M, and the capitate C bones into the correct orientation by sliding the bone attachment members 40 within the oblong distal and proximal attachment openings 22, 12.

For example, by moving the wrist fusion plate 2 in a distal direction with a bone attachment member 40 provided in the oblong proximal portion attachment opening 12, the flexion of the wrist can be reduced, because the angle of the capitate C with respect to the radius R can be reduced. In contrast, by moving the wrist fusion plate 2 in a proximal direction with a bone attachment member 40 provided in the oblong proximal portion attachment opening 12, the flexion of the wrist can be increased, by increasing the angle of the capitate C with respect to the radius R.

Because the oblong distal and proximal attachment openings 22, 12 are provided elongated in directions perpendicular to each other, the position of the bone attachment member 40 within each of the oblong distal and proximal attachment openings 22, 12 can be individually adjusted, without (necessarily) affecting the position of the bone attachment member 40 in the other oblong attachment opening. Thereby, fine adjustment of each of the bone attachment members 40 in the oblong openings can be conducted so as to individually adjust the position of the metacarpal M and the inclination of the capitate C. That is, the freedom of adjustment of the metacarpal M provided by the oblong distal portion attachment opening 22 does generally not negatively affect the adjustment ability provided by the oblong proximal portion attachment opening 12, and vice versa. Therefore, a uniquely adaptable wrist fusion plate 2 is provided, whereby the surgeon can easily and quickly implant the wrist fusion plate 2 and can finely and individually tune both wrist flexion and metacarpal positioning, such that maximum usability and minimum pain are experienced by the patient.

The surgeon can adjust the desired orientation of the metacarpal M by sliding the bone attachment member 40 within the oblong distal portion attachment opening 22 as discussed with respect to the first embodiment. As also discussed with respect to the oblong distal portion attachment opening 22 of the first embodiment, the oblong proximal portion attachment opening 12 may be configured to receive a bone attachment member 40 having a diameter that is identical to the diameter of the bone attachment members 40 configured to be received by the circular proximal portion attachment openings 11. Alternatively, the diameter of the oblong proximal portion attachment opening 12 may be configured to receive a bone attachment member 40 having a diameter that is smaller than the diameter of the bone attachment member 40 configured to be received by the circular proximal portion attachment openings 11. For example, the oblong proximal portion attachment opening 12 may be configured to receive a bone attachment member 40 having a diameter of approximately 2.7 mm. Generally, the oblong proximal portion attachment opening 12 may have a diameter within a range of approximately 2.0 to 3.5 mm. Because the oblong proximal portion attachment opening 12 is provided to allow a surgeon to provisionally place the wrist fusion plate 2 with respect to the radius R, while final fixation of the wrist fusion plate 2 with respect to the radius R is provided by the circular proximal portion attachment openings 11, the diameter of the bone attachment member 40 necessary to obtain proper provisional placement of the wrist fusion plate 2 with respect to the radius R, while still allowing sliding of the bone attachment member 40 within the oblong proximal portion attachment opening 12, may be smaller than that necessary for permanent fixation of the proximal portion to the radius R. By sizing the bone attachment members 40 to be as small as possible, patient pain and recovery time can be reduced.

A third embodiment of a wrist fusion plate 3 will now be described with respect to FIG. 4. Elements of the third embodiment that are identical or similar as those described with respect to the first and second embodiments are not specifically discussed. Each of the features and alternatives described with respect to the first and second embodiments are applicable to and can be combined with the features of the third embodiment.

Figure 4:
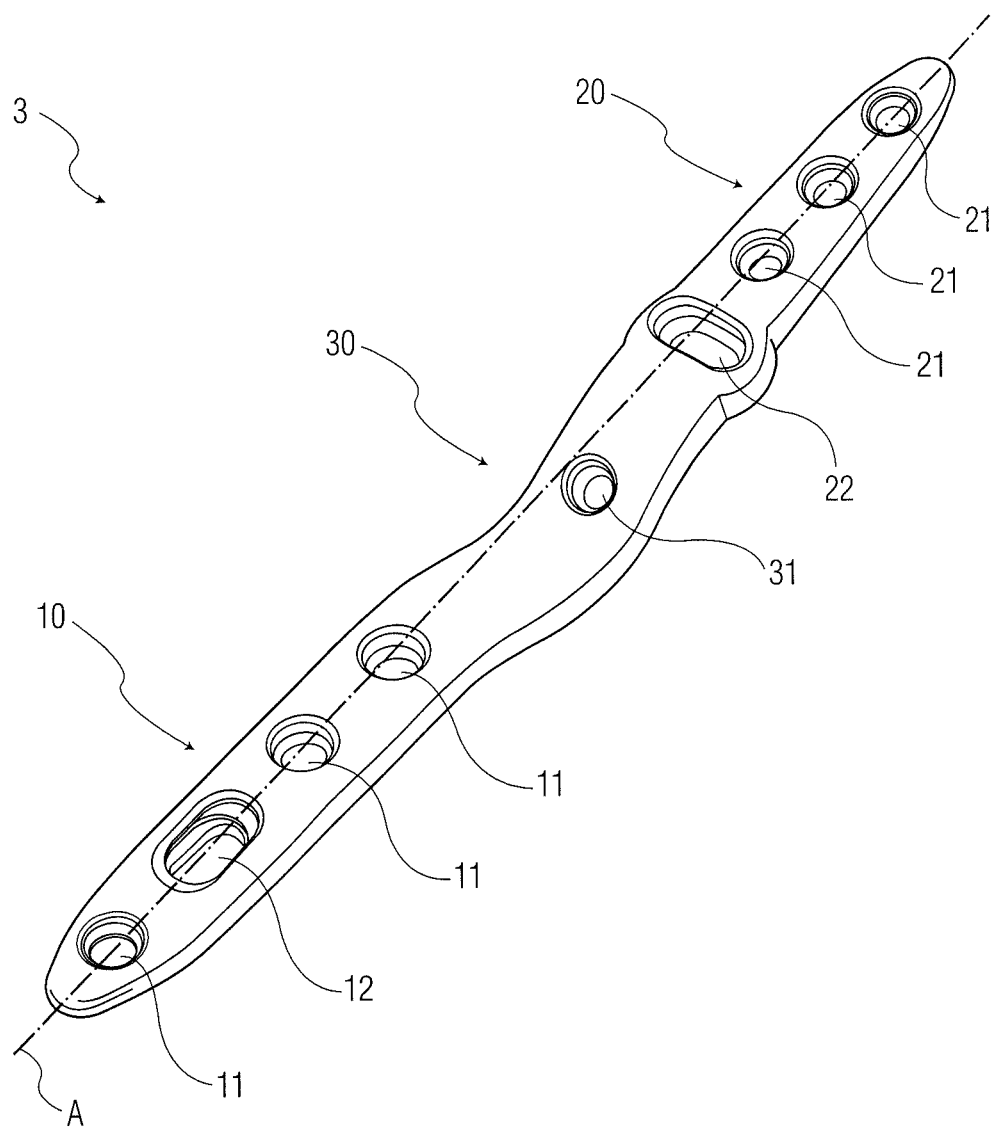
FIG. 4 is a perspective view showing a third embodiment of the wrist fusion plate.

As illustrated in FIG. 4, the wrist fusion plate 3 of the third embodiment is similar to the wrist fusion plate 2 of the second embodiment, except that the wrist fusion plate 3 of the third embodiment has a shorter bend in the central portion 20. As a result, the radial central portion attachment opening 32 is not provided, and, instead, a further proximal portion attachment opening 11 is provided and positioned to be attached to a distal-most position on a dorsal surface of the radius R.

The length of the proximal portion 10 may generally be within a range of approximately 40 to 50 mm. The length of the distal portion 20 may generally be within a range of approximately 35 to 40 mm. The length of the central portion 30 may generally be within a range of approximately 30 to 40 mm. More specifically, the length of the central portion 30 which inclines downwardly from the proximal portion 10 and may generally be within a range of approximately 15 to 20 mm, while the length of the central portion 30 which inclines downwardly from the distal portion 20 and may generally be within a range of approximately 15 to 20 mm.

The method of implanting the wrist fusion plate 3 of the third embodiment is the same as the method of implanting the wrist fusion plate 2 of the second embodiment, except that the bone attachment member 40 provided into the radial central portion attachment opening 32 onto a distal surface of the radius R is not provided, and, instead, a bone attachment member 40 may optionally be provided to a distal most position on a dorsal surface of the radius R through the distal-most proximal portion attachment opening 11.

The wrist fusion plate 3 of the third embodiment may be appropriate for use in patients having smaller wrists, which cannot accommodate the full central portion bend of the wrist fusion plates 1, 2, of the first and second embodiments. The advantages obtained by the wrist fusion plate 3 of the third embodiment are the same as those achieved by the wrist fusion plate 2 of the second embodiment.

A fourth embodiment of a wrist fusion plate 4 will now be described with respect to FIG. 5. Elements of the fourth embodiment that are identical or similar as those described with respect to the first through third embodiments are not specifically discussed. Each of the features and alternatives described with respect to the first through third embodiments are applicable to and can be combined with the features of the fourth embodiment.

Figure 5:
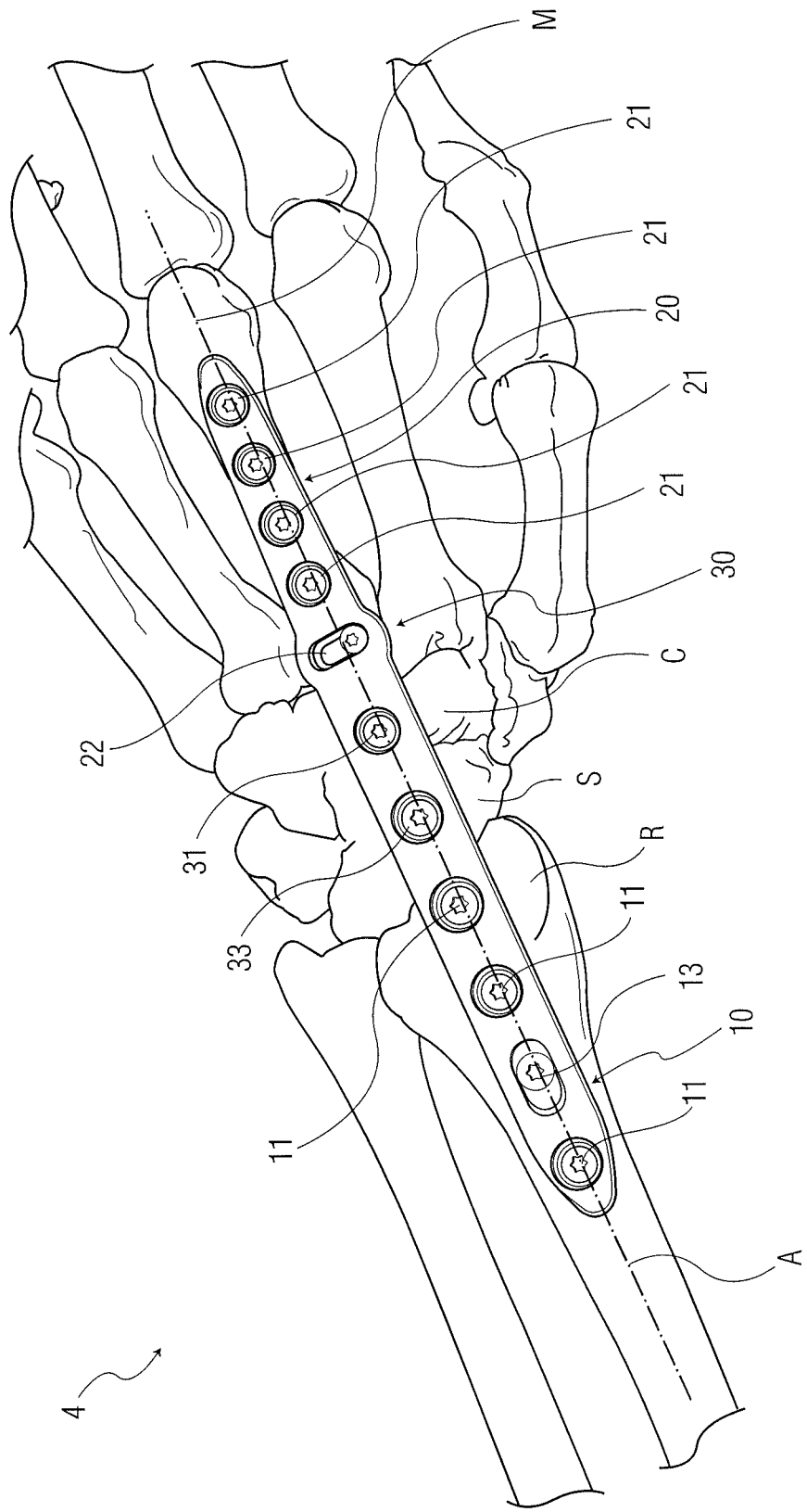
FIG. 5 is a perspective view showing a fourth embodiment of the wrist fusion plate.

As illustrated in FIG. 5, the wrist fusion plate 4 of the fourth embodiment is similar to the wrist fusion plates 2, 3 of the second and third embodiments, except that the wrist fusion plate 4 of the fourth embodiment has a central portion 30 that is not bent. That is, the wrist fusion plate 4 has a generally straight (and substantially planar) configuration, extending along the longitudinal axis A without any out-of-plane bending as in the previous embodiments.

As for the wrist fusion plate 4 of the fourth embodiment, a further attachment opening 33 is provided in the central portion, positioned so as to be attached to a scaphoid S of the wrist. Additionally, a larger number of distal portion attachment openings 21 may be provided. In the illustrated example, five distal portion attachment openings 21, 22 are provided, positioned to be attached to the metacarpal M. Of the five distal portion attachment openings 21, 22, one is an oblong distal portion attachment opening 22, described with respect to the first through third embodiments, and four are circular distal portion attachment openings 21.

The straight plate 4 of the fourth embodiment may be particularly suited to patients having a severely deformed wrist bone structure, such that a proper wrist flexion cannot be achieved. Alternatively, if the carpal bones are deformed or malformed such that wrist flexion can be achieved with a straight plate, with or without assistance of bone grafts, the straight plate may provide a better fixation of the wrist than the wrist plates 1, 2 and 3 having the bent central portions 30 as described with respect to the first through third embodiments.

By providing the oblong proximal portion attachment opening 12, the position of the wrist plate 4 with respect to the scaphoid S and capitate C can be finely adjusted, and the desired positions of fixation to these bones necessary to achieve the desired fixed orientation of the scaphoid S and capitate C can be achieved easily, without the need to replace provisionally attached bone attachment members 40.

The length of the proximal portion 10 may generally be within a range of approximately 40 to 50 mm. The length of the distal portion 20 may generally be within a range of approximately 35 to 40 mm. The length of the central portion 30 may generally be within a range of approximately 30 to 40 mm.

Figure 6:
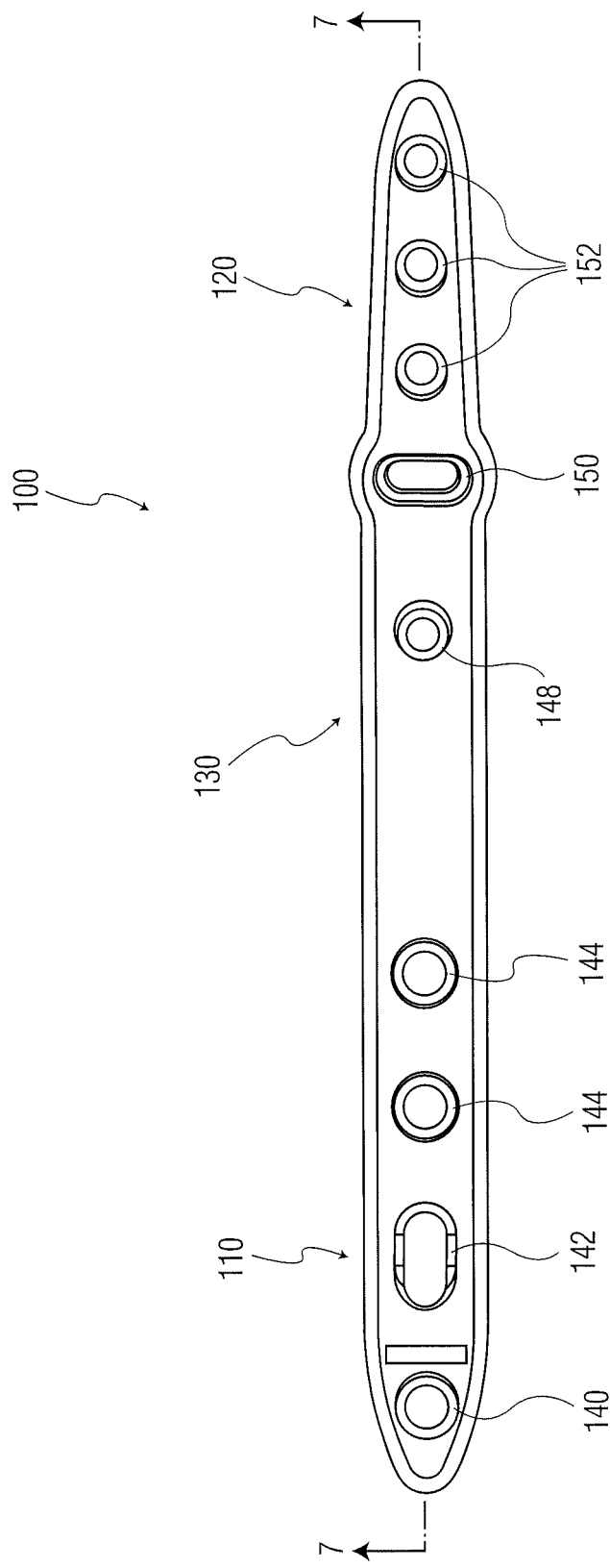
FIG. 6 is a top view of a bone plate of the present invention.

Referring to FIG. 6 there is shown a top view of a wrist plate generally denoted as 100 having a proximal portion 110, a central portion 130 and a distal portion 120 when implanted on a wrist. Proximal portion 110 includes a proximal most locking hole 140, a compression slot 142 and a pair of locking holes 144 located distally of slot 142 when implanted. Central section 130 includes a threaded locking hole 148 proximal of a slot 150 which slot extends perpendicular to a longitudinal axis of bone plate 100. Distal plate portion 120 includes three locking holes 152. These holes are aligned with the metacarpal bone as is slot 150. Hole 148 is aligned so that a screw may be inserted in a carpal bone. All the holes may be centered on the central longitudinal axis of the plate 100.

Figure 7:
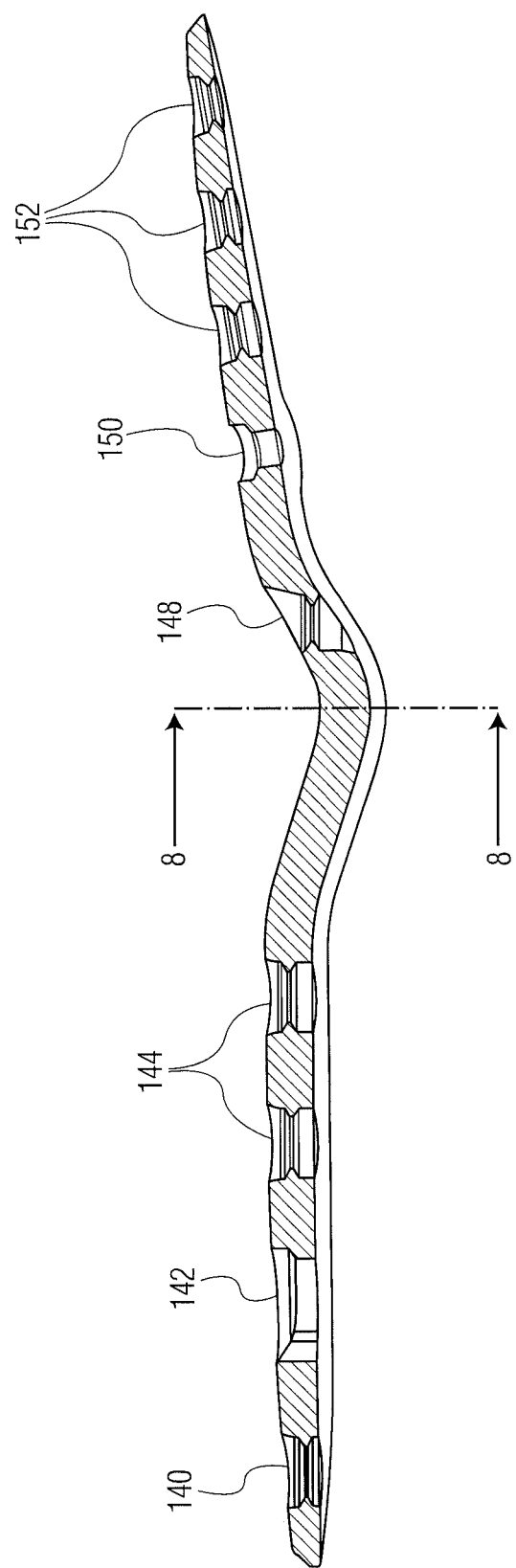
FIG. 7 is a cross-sectional view along lines VII-VII of FIG. 6 showing in the cross-sections of the various bores through the bone plate.

Referring to FIG. 7 there is shown a cross-sectional view of bone plate 100 along the central longitudinal axis bisecting all the slots and holes including the compression slot 142. As can be seen bores 140, 144, 148 and 152 are circular bores having a circumferential flange with a pointed triangular cross-section extending inwardly of the bore for engaging a locking thread on a bone screw, for example a 2.7 or 3.5 millimeter bone screw.

Figure 8:
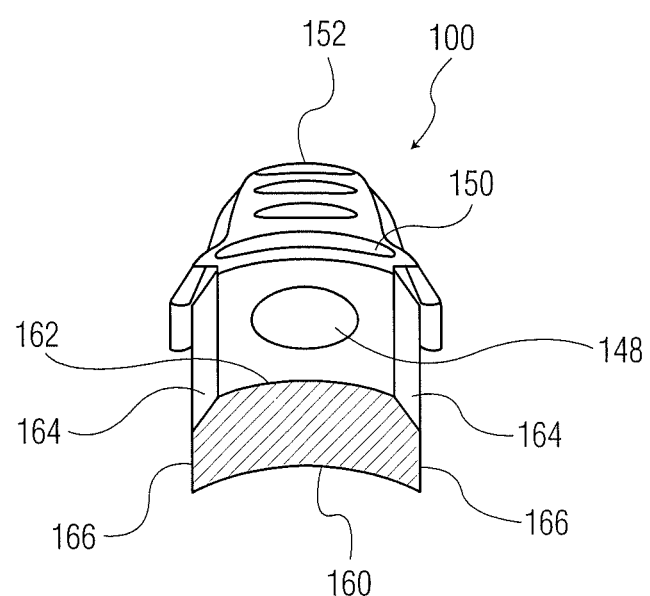
FIG. 8 is a cross-sectional view through lines VIII-VIII of FIG. 7.
Figure 9:
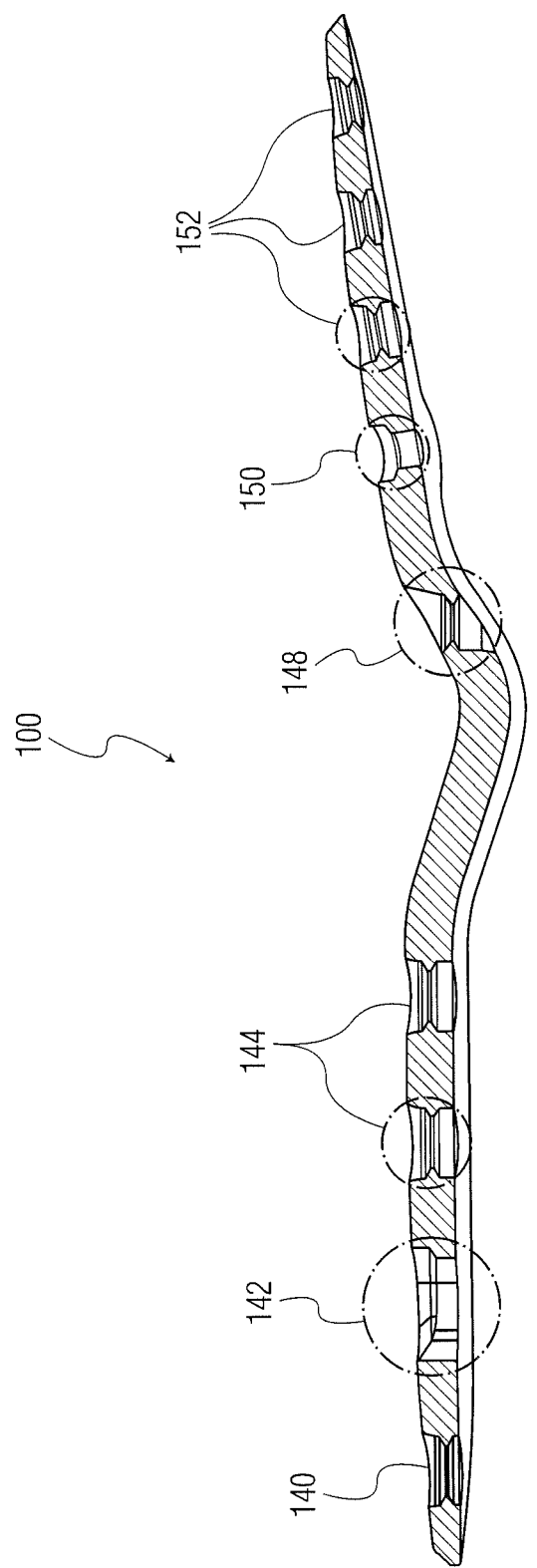
FIG. 9 is a cross-sectional view showing the various different opening through the bone plate of the present invention.
Figure 10:
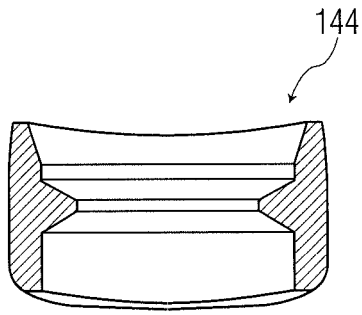
FIGS. 10-16 show enlarged details of the various apertures and openings of FIG. 9 with FIG. 15 showing a top view of the compression slot which is aligned with the longitudinal axis of the bone plate.
Figure 11:
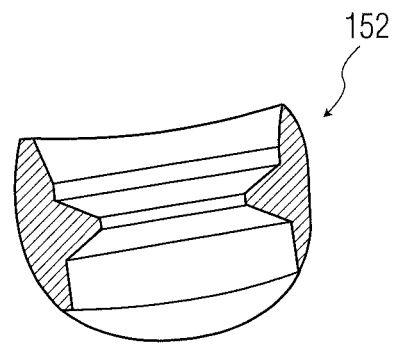
Figure 12:
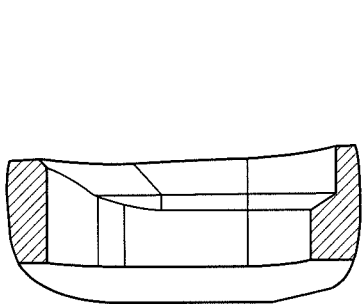
Figure 13:
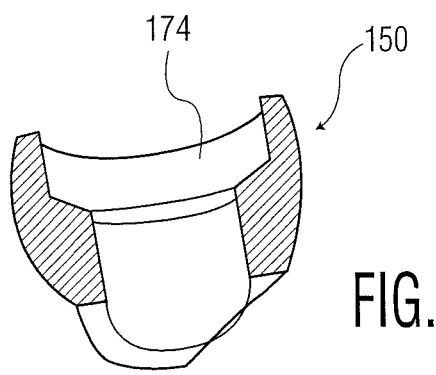
Figure 14:
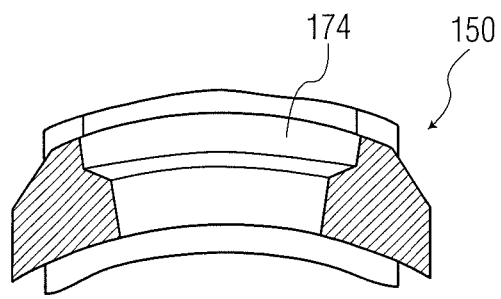
Figure 15:
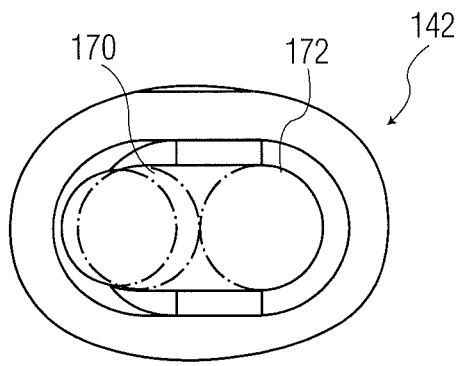
Figure 16:
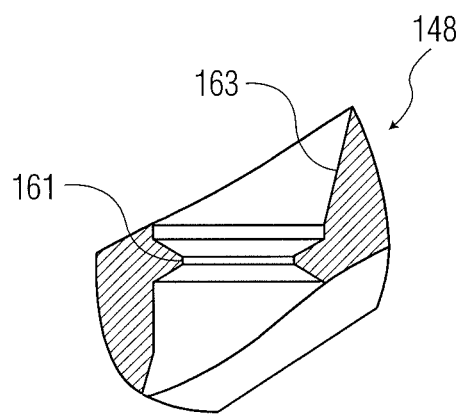

Referring to FIG. 8 there is shown a cross-section of the plate 100 along lines 8-8 of FIG. 7 showing an arcuate bone contacting surface 160 for contacting a wrist bone. Surface 160 is spaced from an arcuate outer surface 162 by angled planar side surface 164 and planar side surface 166. Referring to FIG. 9 there is shown the bone plate cross-section of FIG. 7 with the five different shaped holes 140, 142, 144, 148, 150 and 152 shown. These holes are enlarged in FIGS. 10-14 and 16. Referring to FIG. 10 there is shown an example of the two circular openings 144 with FIG. 11 showing a cross-section of the three bores 152. FIG. 12 shows a cross-sectional view of the compression hole 142 with FIG. 15 showing a top view of compression hole 142. FIG. 13 shows a cross-sectional view along the longitudinal axis of the plate of elongated gliding slot 150 with FIG. 14 showing a cross-sectional view of opening 150 extending along an axis perpendicular to the longitudinal axis of the bone plate. A cross-sectional view of opening 148 is shown in FIG. 16. Compression hole 142 is a typical compression hole allowing either compression when the screw is inserted at location 170 in the slot as shown in FIG. 15 or non-compression if a screw is inserted in location 172 of FIG. 15. As can be seen from FIGS. 13 and 14 the elongated gliding slot 150 allows a screw having a head located in area 174 of FIG. 13 located in any location along the length of the slot.

Referring to FIG. 16 there is shown carpal screw bore 148 again with a circumferential triangularly shaped ring 161 for engaging a locking thread on a bone screw. Typically the flanks of the circumferential inwardly extending triangularly shaped protrusion are angled at approximately 60° on the upper and lower flanks with the bores typically having a conical inlet on the other surface of the bone plate angled at about 15° with respect to the central axis of the through bore. The inwardly projecting ring 161 is typical for the other locking holes, for example holes 144 and 152.

The central section 130 of plate 100 may have a curved portion with a convex bone contacting surface and a concave outer surface. Alternately the plate may be planar. The curve may have a radius of about 20 cm.

Figure 17:
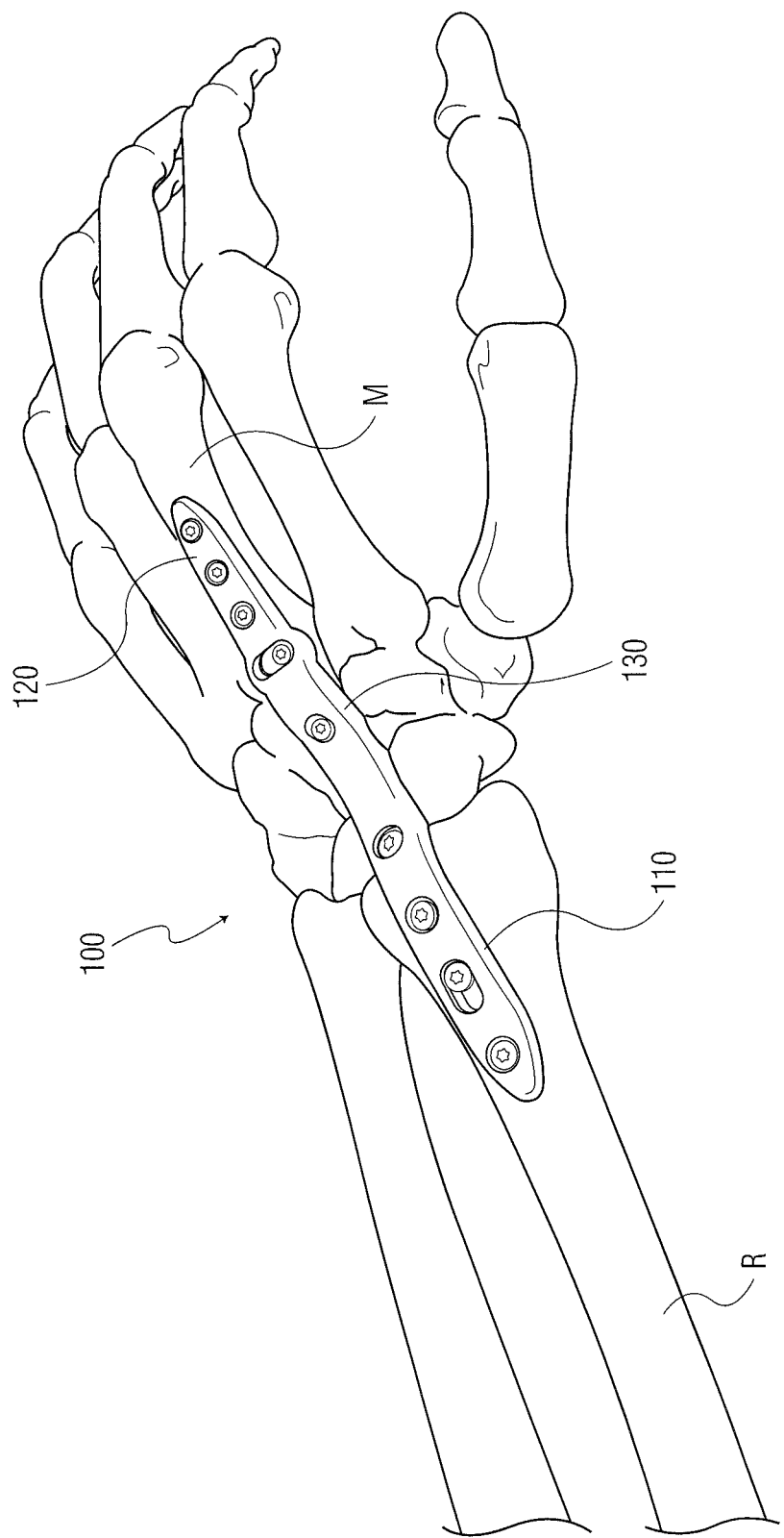
FIG. 17 shows a bone plate of FIGS. 6-16 implanted on a wrist in a similar manner as shown in FIG. 5.

Referring to FIG. 17 there is shown plate 100 mounted on a radius R at its proximal end 110 and to a metacarpal bone M at its distal end 120 into a carpal bone C in its central portion 130.

The method of implantation of the plate 100 utilizes a k wire inserted through proximal most hole 140 as an initial location of the bone plate. Obviously the plate may be rotated about the implanted k wire. A 3.5 mm bone screw is then inserted into the compression hole 142 and left loose. A 2.7 mm bone screw is placed in the guiding hole 150 and preferably directed into the metacarpal with the screw in a neutral position and also left loose. The hand is adjusted for rotational position and the 2.7 mm screw and gliding hole 150 is tightened. The three locking screws, preferably 2.7 mm, are placed into the metacarpal via locking holes 152. At this point the k wire can be removed from hole 140 and the 3.5 mm compression screw in compression hole 142 is tightened. Locking screws are then inserted into locking holes 144 and tightened. A locking screw is inserted into hole 140 and this is tightened. Lastly a 2.7 mm locking capitate is inserted through locking hole 148.

Having described embodiments of the invention referring to the accompanying drawings, it should be understood that the present disclosure is not limited to those precise embodiments. Various changes and modifications thereof may be made by one skilled in the art without departing from the scope of the claims appended hereto.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A wrist fusion plate configured for fusing a wrist of a patient, comprising:
    a proximal portion comprising at least three proximal portion attachment openings axially aligned along a longitudinal axis of the plate, wherein the proximal portion is adapted to be attached to a radius of a patient by inserting a bone attachment member through the at least one proximal portion attachment opening and into the radius;
    wherein one of the at least three proximal portion attachment openings is an oblong portion attachment opening that is elongated in a direction along the longitudinal axis,
    a distal portion comprising at least four distal portion attachment openings axially aligned along the longitudinal axis and adapted to be attached to a metacarpal of the patient by inserting bone attachment members through the distal portion attachment openings and into the metacarpal;
    a central portion comprising at least one central portion attachment opening aligned on the longitudinal axis and adapted to be attached to a carpal bone of the wrist by inserting a bone attachment member through the central portion attachment opening,
    wherein the central portion comprises a distal central portion which inclines in a palmar direction from the distal portion, and a proximal central portion which inclines in a palmar direction from the proximal portion such that the central portion is bent in a palmar direction from the longitudinal axis;
    wherein at least the proximal portion and the distal portion extend substantially along the longitudinal axis of the wrist fusion plate; and
    wherein one of the distal portion attachment openings is an oblong distal portion attachment opening that is elongated in a direction substantially perpendicular to the longitudinal axis, the oblong opening is located distally to allow the insertion of a bone attachment member through the oblong opening into a proximal portion of the metacarpal.

2. The wrist fusion plate according to claim 1, wherein the at least one central portion attachment opening adapted to be attached a carpal bone of the patient is adapted to be attached to a capitate of the wrist of the patient.

3. The wrist fusion plate according to claim 1, wherein the central portion further comprises a second central portion attachment opening configured to be fixed to a distal surface of the radius of the patient.

4. The wrist fusion plate according to claim 1, wherein the central portion is substantially straight, and wherein the distal, proximal, and central portions extend substantially along the longitudinal axis.

5. The wrist fusion plate according to claim 4, wherein the central portion comprises two central portion attachment openings adapted to be attached to carpal bones,
    wherein a first central portion attachment opening is configured to be attached to a capitate of the wrist of the patient, and
    wherein a second central portion attachment opening is configured to be attached to a scaphoid of the wrist of the patient.

6. The wrist fusion plate of claim 1, wherein the oblong proximal portion attachment opening has a length in the direction parallel to the longitudinal axis within a range of approximately 3.0 mm to 5.0 mm.

7. The wrist fusion plate according to claim 1, wherein the oblong distal portion attachment opening has a length in the direction perpendicular to the longitudinal axis within a range of approximately 2.0 mm to 4.0 mm.

8. The wrist fusion plate according to claim 1, wherein the distal portion attachment openings other than the oblong distal portion attachment opening are circular distal portion attachment openings having a diameter within a range of approximately 2.0 to 3.5 mm.

9. The wrist fusion plate according to claim 1, wherein one or more proximal portion attachment openings other than the oblong proximal portion attachment opening have a diameter within a range of approximately 2.7 to 4.0 mm.

10. The wrist fusion plate according to claim 1, wherein a length of the oblong distal portion attachment opening is greater than a width of the distal portion adjacent to the oblong distal portion attachment opening, and
    wherein protrusions are provided to the distal portion in the region of the oblong distal portion attachment opening to allow the distal portion to accommodate the oblong distal portion attachment opening.

11. The wrist fusion plate according to claim 1, wherein at least one of the attachment openings is sunken.

12. The wrist fusion plate according to claim 11, wherein the at least one attachment opening is sunken so as to receive the bone attachment member such that the bone attachment member protrudes by an amount less than a thickness of a head portion of the bone attachment member or does not protrude over a dorsal surface of the wrist fusion plate when implanted onto the wrist of the patient.

13. A method of implanting a wrist fusion plate comprising:
    obtaining a wrist fusion plate having a central longitudinal axis, a proximal portion comprising at least three proximal portion attachment openings, a distal portion comprising at least four distal portion attachment openings, a central portion comprising at least one central portion attachment opening wherein the proximal portion and the central portion attachment openings are substantially centered along the central longitudinal axis of the wrist fusion plate, and wherein the distal portion attachment openings are centered along the central longitudinal axis and wherein one of the distal portion attachment openings is an oblong opening elongated in a direction substantially perpendicular to the central longitudinal axis, the oblong opening is located adjacent a proximal portion of the metacarpal; and
    wherein one proximal portion attachment opening is an oblong opening elongated along the central longitudinal axis;
    implanting a first bone attachment member into the metacarpal through the oblong distal portion attachment opening;
    implanting a second bone attachment member into a radius through at least one proximal portion attachment opening;
    adjusting the orientation of the metacarpal with respect to the radius by sliding the first bone attachment member within the oblong distal portion attachment opening; and
    implanting a third bone attachment member through the distal portion attachment opening that is not the oblong distal portion attachment opening into the metacarpal.

14. The method as set forth in claim 13, further comprising:
    inserting a fourth bone attachment member into the radius through the oblong proximal portion attachment opening;

adjusting an amount flexion of the wrist of the patient by sliding the fourth bone attachment member within the oblong proximal portion attachment opening; and inserting a bone attachment member through the central portion attachment opening into a wrist carpal.

15. A method of implanting a wrist fusion plate comprising:

obtaining a bone plate having a distal and a proximal portion defining a longitudinal axis, the proximal portion having three apertures centered on the longitudinal axis extending from an outer surface to a bone facing surface with one aperture being an oblong aperture elongated along the plate longitudinal axis, the distal portion having four apertures centered on the longitudinal axis including an elongated aperture extending from an outer surface to a bone facing surface, the aperture elongated in a direction transverse to the longitudinal axis and capable of being located on a proximal portion of a metacarpal;

placing the bone facing bone plate surface of the distal portion adjacent the metacarpal bone of a patient and the bone facing surface of the proximal portion adjacent a radius of the patient;

inserting a bone fastener through the elongate aperture in the plate distal portion and into the proximal portion of the metacarpal bone and adjusting the orientation of the metacarpal with respect to the radius by sliding the bone fastener along the elongate aperture of the distal portion in a direction transverse to the axis;

inserting a bone fastener through the aperture in the bone plate proximal portion and into the radius; and wherein the bone plate further comprises a central portion located intermediate the distal and proximal portions, the central portion having a substantially convex bone facing surface and a substantially concave outer surface, the convex bone facing surface placed over a carpal bone of the wrist, the central portion having an aperture centered on the longitudinal axis.

16. The method as set forth in claim 15 wherein an aperture extends from the concave outer surface to the convex inner surface of the central portion.

\* \* \* \* \*